United States Patent [19]

Manwaring

[11] Patent Number: 4,739,771

[45] Date of Patent: Apr. 26, 1988

[54] THERMAL METHOD AND APPARATUS FOR MEASURING ORGAN BLOOD PERFUSION

[76] Inventor: Kim Manwaring, 7919 E. Vista Dr., Scottsdale, Ariz. 85253

[21] Appl. No.: 831,980

[22] Filed: Feb. 20, 1986

[51] Int. Cl.$^4$ .............................................. A61B 5/02
[52] U.S. Cl. .................................... 128/691; 128/748
[58] Field of Search ............... 128/691, 692, 748, 713, 128/736

[56] References Cited

U.S. PATENT DOCUMENTS

| | | |
|---|---|---|
| 1,691,600 | 11/1928 | Brush, Jr. et al. |
| 2,728,337 | 12/1955 | Guillemin, Jr. ........................ 128/2 |
| 2,892,347 | 6/1959 | Laprand ............................... 73/204 |
| 3,138,025 | 6/1964 | Fingerson ............................ 73/339 |
| 3,347,224 | 10/1967 | Adams .............................. 128/2.05 |
| 3,405,708 | 10/1968 | Webster, Jr. ....................... 128/2.05 |
| 3,438,253 | 4/1969 | Kuether et al. ...................... 73/204 |
| 3,545,428 | 12/1970 | Webster, Jr. ....................... 128/2.05 |
| 3,595,079 | 6/1971 | Grahn ................................. 73/204 |
| 3,627,207 | 11/1971 | Sinclair ............................... 128/2.05 |
| 3,789,831 | 2/1974 | Kopaniky et al. ................... 128/692 |
| 3,803,913 | 4/1974 | Tracer ................................. 73/204 |
| 3,821,643 | 7/1974 | Bostick et al. ....................... 324/65 |
| 4,059,982 | 11/1977 | Bowman .............................. 73/204 |
| 4,083,243 | 4/1978 | Cochran, Jr. ......................... 73/204 |
| 4,090,406 | 5/1978 | Rodder ................................ 73/204 |
| 4,236,527 | 12/1980 | Newbower et al. ................... 73/204 |
| 4,240,441 | 12/1980 | Khalil ................................. 128/692 |
| 4,354,504 | 10/1982 | Bro ..................................... 128/736 |
| 4,403,615 | 9/1983 | Hoehner ............................. 128/692 |
| 4,419,999 | 12/1983 | May, Jr. et al. ..................... 128/691 |
| 4,479,795 | 10/1984 | Mastacich et al. ................... 604/53 |
| 4,494,350 | 1/1985 | Blazek et al. ....................... 128/691 |
| 4,569,355 | 2/1986 | Bitterly ............................... 128/692 |
| 4,572,206 | 2/1986 | Geddes et al. ...................... 128/692 |
| 4,576,035 | 3/1986 | Hooven et al. ..................... 128/748 |
| 4,600,017 | 6/1986 | Schroeppel ......................... 128/675 |

FOREIGN PATENT DOCUMENTS

| | | | |
|---|---|---|---|
| 3048192 | 8/1982 | Fed. Rep. of Germany ...... 128/691 |
| 8301279 | 11/1984 | Netherlands ........................ 128/691 |
| 556786 | 7/1977 | U.S.S.R. ............................. 128/691 |
| 923520 | 4/1982 | U.S.S.R. ............................. 128/692 |
| 1039482 | 9/1983 | U.S.S.R. ............................. 128/713 |

OTHER PUBLICATIONS

"Automated Cardiac Output Determination by Indication Dilution in a Computerized Patient Monitoring System", by Mendler et al; Conference on Computers in Cardiology; Potterdam, Netherlands, 9/24–10/1; 1977, pp. 247–249.

(List continued on next page.)

Primary Examiner—Lee S. Cohen
Assistant Examiner—David Shay
Attorney, Agent, or Firm—Cahill, Sutton & Thomas

[57] ABSTRACT

A ventriculostomy tube having a semi-rigid body and a fluid transmissive passageway extending from a first end to a second end of the tube is inserted through an aperture in a skull. The first end of the tube includes a port for establishing fluid communication between the passageway and a fluid space within the brain tissue surrounding the tube known as the lateral ventricle. By establishing fluid communication between the lateral ventricle of the brain and the second end of the tube, the ventriculostomy tube enables intracranial pressure to be continuously monitored. An electric current is passed through electrical leads extending along the length of the ventriculostomy tube to a thermistor which is secured to the exterior surface of the tube at a first elevation to measure the temperature of the brain tissue at a first elevation. Control means is electrically coupled to the thermistor and provides electrical energy to establish a temperature gradient between the thermistor and the adjacent brain tissue to transfer heat from the thermistor into the brain tissue. Measurement means is coupled to the control means to measure the flow of electrical energy through the thermistor and to compute the thermal conductivity of the brain tissue and blood adjacent to the thermistor to determine local cerebral blood flow (LCBF).

17 Claims, 2 Drawing Sheets

U.S. PATENT DOCUMENTS

"Accurate Measurement of Skin Blood Flow by a Thermal Conductance Method", by Challoner; Med & Biol Eng., vol. 13, No. 2, pp. 196–201, Mar. 1975.

"A Spherical Heated Thermocouple Probe for Perfusion Measurements", by Johnson et al, Conference: 1978 Advances in Bioengineering, San Francisco, CA USA; Dec. 10–15, 1978.

"In Vivo Measurement of Brain Blood Flow in the Cat", by J. Petrofsky; IEEE Trans on Biomed. Eng., vol. BME-26, No. 8, Aug. 1979.

"Measurement of Focal Brain Blood Flow Transients: A Technique Using Heat Transfer Properties", by T. Adams et al; Conference: 1978 Advances in Bioengineering, San Francisco, CA USA; Dec. 10–15, 1978.

THERMAL METHOD AND APPARATUS FOR MEASURING ORGAN BLOOD PERFUSION

BACKGROUND OF THE INVENTION

1. Field of the Invention

This invention relates to instrumentation and a technique for measuring local cerebral blood flow and intracranial pressure, and more particularly, to a ventriculostomy tube having the capability of simultaneously and continuously measuring on a real time basis both intracranial pressure and local cerebral blood flow.

2. Description of the Prior Art

Ventriculostomy tubes have been used for many years to measure intracranial pressure to assist in diagnosing and treating various pathologic conditions of the brain. This instrument is inserted into a ventricle in the brain through a drilled aperture in the skull to directly and continuously measure the absolute value of intracranial pressure at a given site.

Different types of instrumentation have been developed to measure local cerebral blood flow in the brain. Generally, such instrumentation typically utilizes multiple sensors which are inserted into the brain at two different sites through two separate drilled apertures or rely on a single brain probe and a separate probe inserted into a blood vessel at a site remote from the brain. None of these prior art devices provides for simultaneous measurement of both intracranial pressure and local cerebral blood flow (LCBF) or utilizes an instrument capable of being inserted through a single aperture in the skull even though it is generally recognized that the probability of brain injury is substantially enhanced by the insertion of multiple probes at multiple brain sites. In addition, some prior art devices provide a delayed response to changes in local cerebral blood flow or provide relative rather than absolute LCBF readouts.

SUMMARY OF THE INVENTION

It is therefore a primary object of the present invention to provide an instrument which can be inserted through a single aperture in the skull for simultaneously and continuously monitoring on a real time basis both intracranial pressure and local cerebral blood flow at one or more elevations within the brain.

Another object of the present invention is to provide an instrument capable of providing a fast response, real time measurement of local cerebral blood flow at a well defined, highly localized site within the brain.

Yet another object of the present invention is to provide an instrument capable of providing a continuous real time readout of the local cerebral blood flow at two spaced apart sites within the brain, one of which could be located within brain white matter while the other could be located within the brain gray matter.

Still another object of the present invention is to provide an instrument incorporating heat transfer means which can be mounted on the exterior surface of a ventriculostomy tube without significantly increasing the physical dimensions of that tube for enabling the instrument to simultaneously measure both intracranial pressure and local cerebral blood flow.

Still another object of the present invention is to provide an instrument which can provide a continuous, highly accurate readout of the true value of the local cerebral blood flow at a defined brain site for an extended period of time without frequent recalibration.

Still another object of the present invention is to provide an instrument for measuring the true value of local cerebral blood flow which can be periodically recalibrated by injecting a small value of fluid into an artery feeding the brain.

Still another object of the present invention is to provide an instrument for measuring the local cerebral blood flow that includes a fast response time and a high sensitivity level which enables the instrument to measure the effect of each individual heart beat on local cerebral blood flow.

Briefly stated, and in accord with one embodiment of the invention, an apparatus for measuring local cerebral blood flow in brain tissue enclosed within a skull includes a catheter having first and second end sections where the second end section extends through an aperture in the skull and penetrates into the brain tissue. Heat transfer means is coupled to the second end section of the catheter for receiving a flow of electrical current, for converting the current into heat energy and for transferring the heat energy into adjacent brain tissue. Control means is electrically coupled to the heat transfer means and provides electrical energy to the heat transfer means to establish a temperature gradient between the heat transfer means and the adjacent brain tissue to thereby transfer heat from the heat transfer means into the brain tissue. Measurement means is coupled to the control means for measuring the flow of electrical energy through the heat transfer means and for computing the thermal conductivity of the brain tissue and flowing blood adjacent to the heat transfer means to determine the local cerebral blood flow.

DESCRIPTION OF THE DRAWINGS

This invention is pointed out with particularity in the appended claims. However, other objects and advantages together with the operation of the invention may be better understood by reference to the following illustrations, wherein:

DESCRIPTION OF THE PREFERRED EMBODIMENT

In order to better illustrate the advantages of the invention and its contributions to the art, a preferred hardware embodiment of the invention will now be described in detail.

Figure 1:
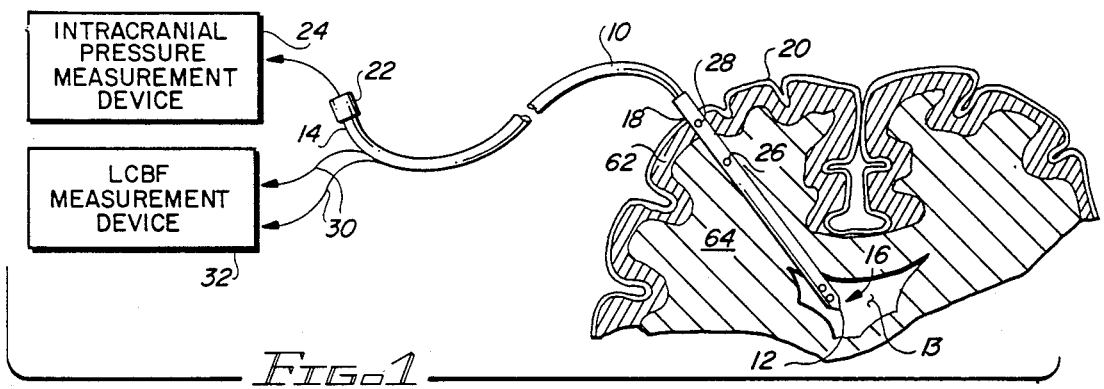
FIG. 1 is a partially cutaway sectional view depicting the ventriculostomy tube plus heat transfer means inserted through an aperture in the skull.

Referring now to FIG. 1, a silastic ventriculostomy catheter or tube 10 is fabricated in a length of between ten to twenty-five centimeters with an outer diameter of approximately 2.4 millimeters. The hollow interior of tube 10 includes a fluid transmissive passageway which extends from a first end designated by reference number 12 to a second end designated by reference number 14. A plurality of circular ports designated generally by reference number 16 are disposed in first end 12 of tube 10 for establishing fluid communication between the lateral ventricle 13 of the brain and the exterior end 14 of the tube 10.

Conventional ventriculostomy tubes of the type described above represent a standard item of instrumentation utilized in neurosurgical procedures. During surgery, an incision is made in the scalp permitting the scalp tissue to be pulled back from the skull. An aperture 18 is then drilled into the skull and first end 12 of ventriculostomy tube 10 is inserted to a depth of several centimeters into the human brain. Cerebrospinal fluid from the ventricular system flows through ports 16 and through the internal passagway in tube 10 to establish fluid communication between the second end 14 and the first end 12 of tube 10. A pressure transducer 22 or equivalent device converts the pressure level sensed at second end 14 into an electrical output signal. This electrical output signal from transducer 22 is coupled to an intracranial pressure measurement device 24 which displays and records real time fluctuations in intracranial pressure (ICP).

Although insertion of the ventriculostomy tube into the brain creates certain risks, this device over a substantial length of time has proven to be comparatively safe and generates information highly usable to neurosurgeons. A major objective of the present invention is to add additional structure to the comparatively safe, frequently used and well-proven ventriculostomy catheter to obtain substantially more data about the condition and function of the brain without inserting other probes into the brain or into other body sites. The availability of real time, continuous measurement of local cerebral blood flow (LCBF) permits a substantially more detailed study and analysis of brain injury or disease, facilitates the timing and scope of surgical or medical intervention and enhances post-treatment results. The present invention therefore relates to the incorporation of a dual-level LCBF measurement device into a ventriculostomy tube to produce an instrument which is capable of continuously measuring in real time both the LCBF at first and second brain elevations as well as the brain intracranial pressure.

Figure 2:
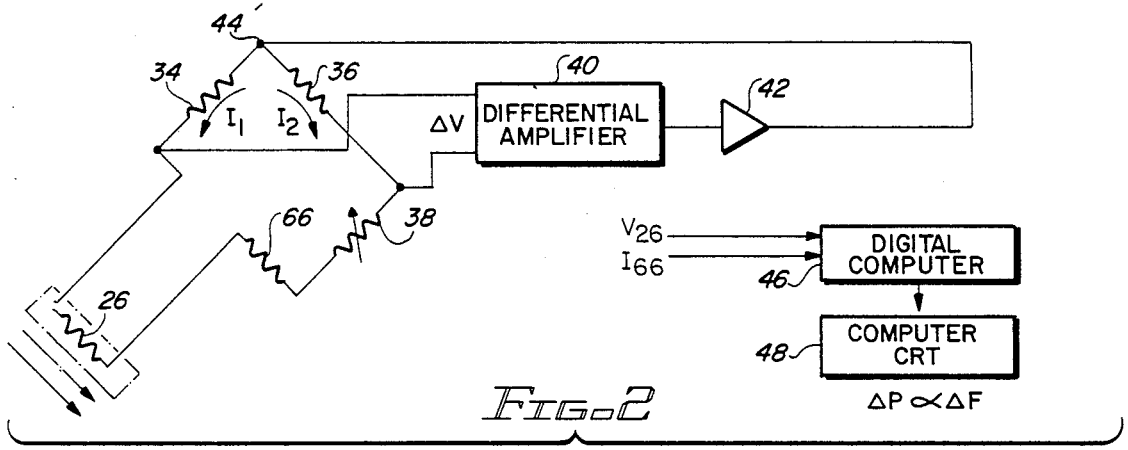
FIG. 2 represents an electrical schematic diagram of an isothermal circuit for measuring local cerebral blood flow (LCBF).

Referring now to FIGS. 1 and 2, a first thermistor 26 and a second thermistor 28 serve as heat transfer means and are coupled respectively at first and second elevations to the exterior wall of ventriculostomy tube or catheter 10. These miniature thermistors have an exterior diameter of approximately 0.20 millimeters and are commercially available from the Thermometrics Company of New Jersey. Silicone sealant or an equivalent adhesive couples thermistors 26 and 28 to the exterior wall of tube 10. Each thermistor includes a two-conductor electrical lead or cable designated generally by reference number 30 which extends upward along the length of tube 10. In the preferred embodiment of the invention, thermistors 26 and 28 are spaced apart by a distance of no less than 10 mm to minimize any inter-thermistor heat transfer effects. Depending on the depth of penetration of the first end 12 of tube 10 into the brain tissue, thermistor 26 may be positioned within the brain grey matter (FIG. 1, reference number 62) while thermistor 28 may be positioned within the brain white matter (FIG. 1, reference number 64). The LCBF in grey matter is generally much higher than LCBF in white matter.

The twin output leads 30 from thermistors 26 and 28 are electrically coupled to an LCBF measurement device designated generally by reference number 32. Measurement device 32 may use either isothermal or isocaloric techniques for computing the real time LCBF. FIG. 2 depicts the preferred embodiment of an isothermal LCBF measurement device while FIG. 3 depicts a circuit for measuring LCBF by means of isocaloric techniques.

Referring now to FIGS. 1 and 2, thermistor 26 forms one leg of a Wheatstone bridge which also includes fixed resistors 34 and 36 and a variable resistor or potentiometer 38. Since thermistors 26 and 28 are both coupled within identical circuits, the discussion below will recite only the function and operation of a single FIG. 2 electronic circuit for isothermally measuring LCBF. The circuit including thermistor 28 is a duplicate of the FIG. circuit.

Figure 4:
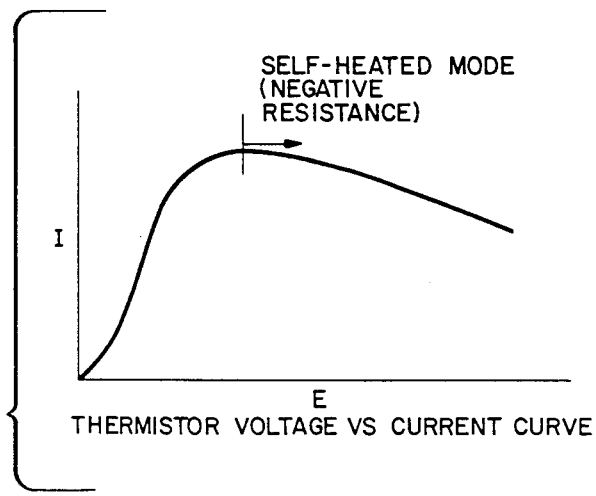
FIG. 4 represents a graphical depiction of the voltage versus current transfer curve of a solid state thermistor.

A thermistor is a semiconductor device the resistance of which varies with temperature. As illustrated in FIG. 4 which plots thermistor voltage versus current, the thermistor transitions into a negative resistance region which is commonly referred to as the self-heated mode when operated in a well-defined current/voltage region. In the self-heated mode, increasing thermistor temperature produces decreasing thermistor resistance and small changes in temperature create very significant changes in thermistor resistance.

Figure 3:
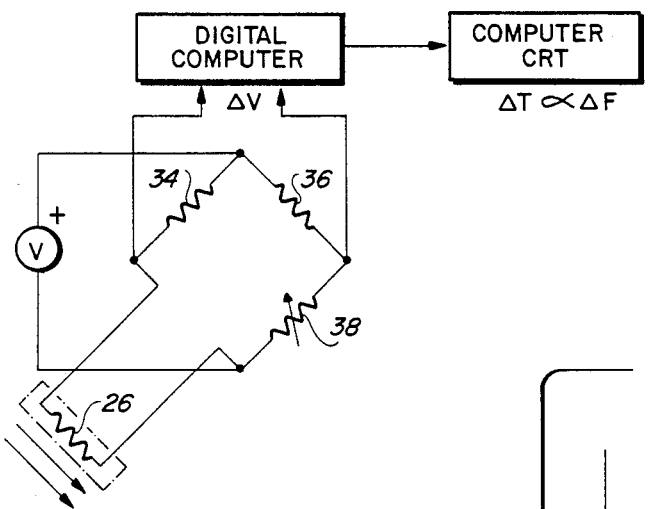
FIG. 3 represents an electrical schematic diagram of an isocaloric version of the present invention for measuring the local cerebral blood flow.

For both the isothermal and isocaloric circuits depicted in FIGS. 2 and 3, the following power equation can be used to compute LCBF which is identified by the term "Qb":

$$P = 0.24 I^2 R = CK\Delta T + \alpha Qb \Delta T \quad (1)$$

This equation holds true where fluid flow is comparatively small as is the case with blood flow within the brain and other body organs. The "CKΔT" term of Equation (1) above is essentially a constant which represents the basal conductivity of a non-perfused (dead) brain. Although this basal conductivity factor does vary somewhat with time, such time-related variations occur at a slow rate and may be comparatively small in magnitude. Over a period of one to two hours, this basal conductivity term remains relatively constant.

In Equation (1), the constant "α" is a function of local vessel geometry in proximity to each heat-dissipating thermistor. The value of "α" remains constant with time at any fixed location within the brain. Since first end 12 of ventriculostomy tube 10 is inserted into and maintained at a fixed site within the brain and maintains thermistors 26 and 28 at a fixed location, the Equation (1) values of "α" for the vessel geometry adjacent to thermistors 26 and 28 are constant but different. During instrument calibration procedures described below, the value of Qb, local cerebral blood flow in Equation (1), is determined allowing determination of the values of "CKΔT" and "α".

The term "ΔT" in Equation (1) refers to the temperature differential or temperature gradient between a given thermistor and the surrounding brain tissue. The "normal" temperature of human brain tissue is approximately 37° C. Since brain tissue temperature changes slowly with time under normal monitoring conditions, the brain temperature can be assumed to be constant for time intervals of from one to two hours.

In the isothermal circuit depicted in FIG. 2, the voltage applied to the Wheatstone bridge is controlled to vary the power (the "P" term in Equation (1)) dissipated by thermistor 26 to maintain the temperature differential between thermistor 26 and the surrounding brain tissue equal to a fixed temperature differential. This fixed temperature differential is maintained at a value of less than 4° C., typically approximately 1° C., to avoid thermal tissue injury. In view of the numerous assumptions stated above relating to "α", "CKΔT" and brain temperature plus the provision of circuitry for maintaining the Equation (1) "ΔT" term equal to a fixed temperature differential, Equation (1) may be substantially simplified to indicate that "Qb" or LCBF varies directly and linearly with changes in power ("P") applied to the Wheatstone bridge. Equation (2) below illustrates this simplified relationship between power and LCBF:

$$\Delta P \alpha Q b \qquad (2)$$

In FIG. 2, differential amplifier 40 senses the voltage differential (ΔV) between resistor 34 and thermistor 26 and between resistor 36 and resistor 38. This voltage differential is amplified by operational amplifier (op amp) 42 which produces a feedback signal to the node designated by reference number 44 in the Wheatstone bridge. This feedback loop varies the power dissipated by thermistor 26 to maintain the thermistor to brain tissue temperature differential equal to the desired fixed temperature differential.

A low value resistor 66 is placed in series with thermistor 26. The input leads to digital computer 46 are coupled to simultaneously sense the voltage across thermistor 26 and the current through resistor 66 which is equal to the current through thermistor 26. Computer 46 then multiples the thermistor voltage and current values to derive thermistor power dissipation which represents the total conductivity of the brain tissue surrounding and located in close proximity to thermistor 26. This power dissipation or total conductivity value enables the computer to calculate LCBF according to Equation (1). The real time LCBF value is then directed to a visual display such as a computer CRT 48 or a strip chart recorder.

As the blood flow across thermistor 26 varies, the FIG. 2 circuit operates to maintain the fixed temperature differential between thermistor 26 and the surrounding brain tissue constant. Increased blood flow past thermistor 26 requires an increased power flow into the thermistor to maintain the desired fixed temperature differential. A decrease in blood flow past thermistor 26 transfers less heat from the thermistor, tending to increase the thermistor temperature and thereby deviate from the desired fixed temperature differential. The FIG. 2 feedback circuit compensates for this decrease in thermistor heat dissipation by reducing the power transferred to the thermistor so that the desired fixed temperature differential is continuously maintained.

A circuit identical to that depicted in FIG. 2 is coupled to thermistor 28 and provides the same LCBF reading at a second brain elevation. Digital computer 46 converts the analog voltage and current signals from the FIG. 2 circuit into digital signals which can be simultaneously processed and displayed as a second real time LCBF reading.

In the preferred embodiment of the invention, a computer sampling rate of from 30 Hz to 100 Hz is used to provide a highly accurate, real time reading of LCBF in proximity to thermistor 26.

Additional steps are required to cause the FIG. 2 isothermal circuit to operate in a calibrated mode where the computer display accurately reflects the true or absolute LCBF in proximity to thermistor 26. In order to accomplish this necessary calibration, thermistor 26 is first operated in a non-heated mode where it functions as a thermometer to accurately measure the temperature of the surrounding brain tissue. Once this measurement has been completed, potentiometer 38 is readjusted to cause thermistor 26 to operate in the heated mode where a fixed temperature differential is esablished such that the temperature of thermistor 26 is maintained at a fixed level above the temperature of the surrounding brain temperature. In this heated mode, heat is continuously transferred from the thermistor into the surrounding brain tissue.

To calibrate the FIG. 2 circuit, approximately one milliliter of a calibration fluid is injected into a blood vessel such as an artery located upstream from the brain. This fluid is typically injected into the carotid artery via a catheter (such as that used for cerebral angiography).

Figure 5A:
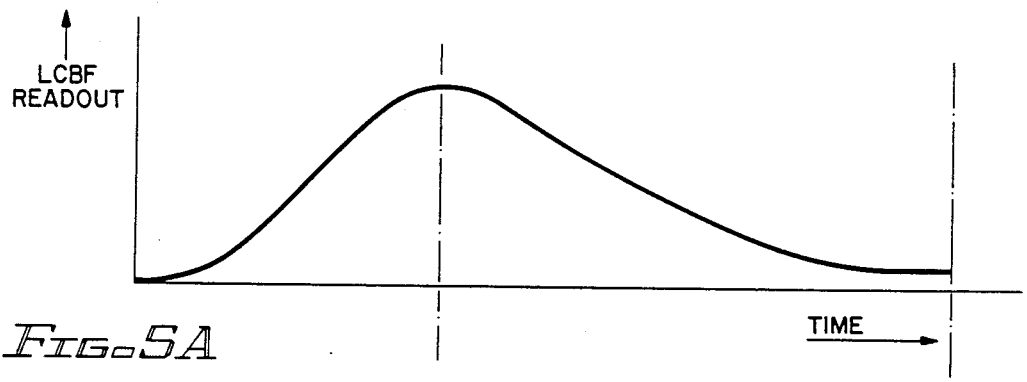
FIG. 5A is a graphical representation of a washout curve depicting the effect of passage of an injected fluid past the LCBF measurement thermistor.
Figure 5B:
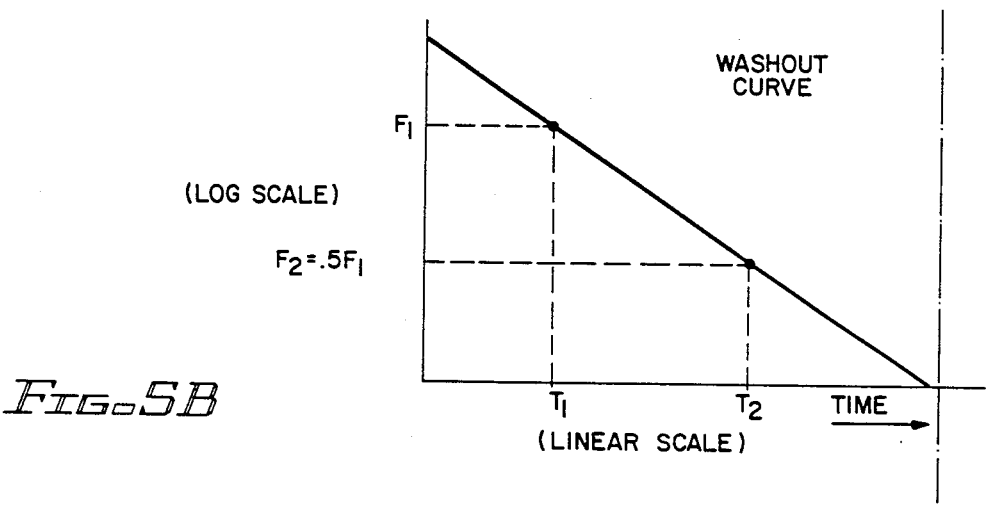
FIG. 5B represents a plot on a semi-log scale of the FIG. 5A LCBF readout commencing with the peak LCBF readout depicted in FIG. 5A.
Figure 6:
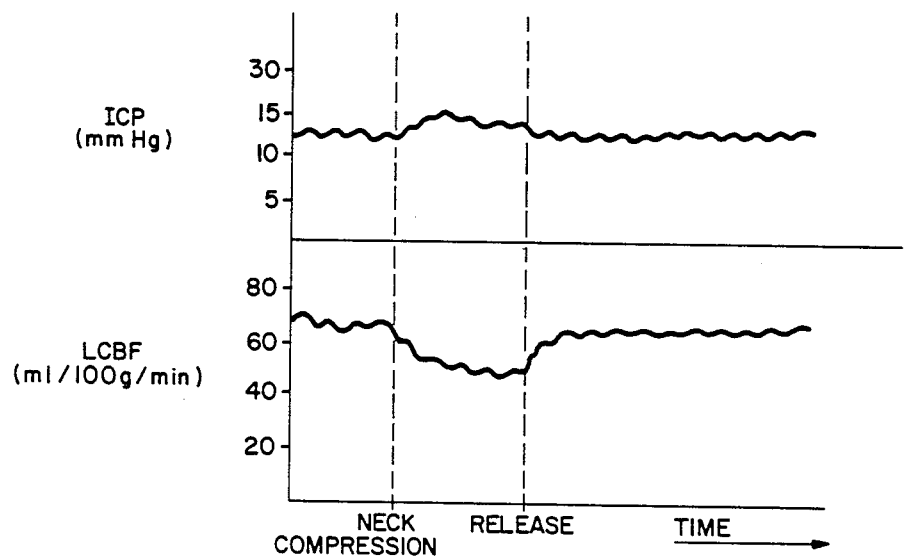
FIG. 6 is a plot of intracranial pressure (ICP) and LCBF versus time before, during and after neck compression. The small magnitude, high frequency fluctuations in both ICP and LCBF are caused by individual heart beats.

Referring now to FIG. 5A, within a few seconds after injection, the injected calibration fluid circulates past thermistor 26. If cold blood is injected, the FIG. 2 circuit senses a decrease in the temperature gradient or Equation (1) ΔT factor and immediately transfers additional power to thermistor 26 to correct the ΔT factor back to the desired 1° C. level. The curve depicted in FIG. 5A corresponds to the passage of the injected cold blood past thermistor 26. The FIG. 5A curve is referred to as a conductivity washout curve and illustrates changes in thermistor power dissipation caused by the approach, the peak value and the departure of the injected cold blood past thermistor 26. The post-peak section of the washout curve can be replotted as illustrated in FIG. 5B on a semi-log scale and provides a highly accurate measurement of the true LCBF past thermistor 26 due to blood flow from that feeding vessel. Equation (3) below may be used to quantify true LCBF:

$$\text{FLOW} = \frac{.693\lambda}{T_{\frac{1}{2}}} \qquad (3)$$

Since the value of "λ" is approximately equal to "1", in Equation (3), the "λ" term may be omitted from the equation. As illustrated in FIG. 5B, the semi-log plot is commenced at the peak value of the washout curve illustrated in FIG. 5A. At a randomly chosen flow rate $F_1$ on the FIG. 5B washout curve, a time $T_1$ is determined. At a second flow rate $F_2$ equal to fifty percent of the value of $F_1$, a time $T_2$ is selected. The time $T_1$ is subtracted from $T_2$ to derive the $T_{\frac{1}{2}}$ term appearing in Equation (3) above. Utilization of the FIG. 5B washout curve in combination with Equation (3) permits rapid computation of a fully calibrated or true LCBF in proximity to thermistor 26.

Comparison of the Equation (3) true LCBF values with the relative LCBF values continuously produced by the FIG. 2 circuit produces a scaling or correction factor which can subsequently be used to calibrate the FIG. 2 circuit by converting the FIG. 2 circuit total conductivity or relative LCBF values to true local cerebral blood flow values as will be described below.

Because $\Delta T$ is maintained at a fixed value, Equation (1) is a linear equation having the general format $y=mx+b$ and can be rewritten and solved for LCBF "or Qb" as follows:

$$Q_b = \frac{.24\ I^2 R}{\alpha \Delta T} - \frac{CK}{\alpha} \quad (1A)$$

where $$m = \frac{.24}{\alpha \Delta T}$$

$$x = I^2 R = P$$

$$b = \frac{-CK}{\alpha}$$

$$y = Q_b$$

Equation 1A can therefore be solved for two different values of LCBF by creating two washout curves under different cerebral blood flow conditions. These two values of LCBF define a line which allows the values of "m" and "b" in Equation 1A to be derived. The computer then continuously monitors the power dissipation of thermistor 26, repetitively solves Equation 1A for LCBF and plots the true LCBF values on a real time basis.

Because of the slow variations in basal conductivity, the slow variations in brain temperature, and the absence of changes in vessel geometry in proximity to thermistor 26, the FIG. 2 circuit will continue to provide accurate real time measurements of LCBF. A calibration of the type described above utilizing the FIG. 5 washout curve should be accomplished every one to two hours to ensure continuing, highly accurate results.

Referring now to FIG. 3, a different circuit is shown for measuring LCBF by utilizing an isocaloric measurement mode. In the isocaloric mode, the power dissipated by thermistor 26 is kept constant such that the change in the "$\Delta T$" factor or temperature gradient becomes directly proportional to changes in LCBF. For operation in the isocaloric mode, Equation (1) is solved for $\Delta T$ as indicated below:

$$\Delta T = \frac{.24 I^2 R}{CK + \alpha Q_b} \quad (4)$$

In Equation (4), the power factor "$0.24 I^2 R$" in the numerator is held constant. The "CK" basal conductivity factor and the "$\alpha$" blood vessel geometry factor remain essentially constant as explained above. Variations in the temperature gradient are therefore inversely related to variations in the "$Q_b$" term or LCBF.

It will be apparent to those skilled in the art that the disclosed LCBF measurement method and apparatus described above may be modified in numerous ways and assume many embodiments other than the preferred forms specifically set out and described above. For example, other transducer devices such as a resistor temperature device could be substituted for thermistors. The spacing between thermistors 26 and 28 may be varied to accomplish any desired measurement objective. In an additional configuration, three or more thermistors could be coupled along a selected length of ventriculostomy tube 10 to provide a substantially enhanced quantity of data regarding continuous, real time measurements of LCBF at various elevations in the brain. Accordingly, it is intended by the appended claims to cover all such modifications of the invention which fall within the true spirit and scope of the invention.

I claim:

1. Apparatus for measuring the true value of local tissue blood flow at a first location in an organ tissue wherein the first location resides outside of the interior of any blood vessels and wherein the organ tissue surrounding and located in close proximity to the first location defines a region of adjacent organ tissue, said apparatus comprising:

a. heat transfer means positionable at the first location and including means for maintaining said heat transfer means fixed at the first location for converting a flow of electrical current into heat energy and for transferring the heat energy into the adjacent organ tissue;

b. control means electrically coupled to said heat transfer means for operating said heat transfer means in a non-self-heating mode to measure the ambient temperature of the adjacent organ tissue and for operating said heat transfer means in a self-heating mode to establish a temperature gradient between said heat transfer means and the adjacent organ tissue to transfer heat energy into the adjacent organ tissue;

c. means coupled to said control means for measuring the heat energy transferred from said heat transfer means into the adjacent organ tissue, for computing the total conductivity of the adjacent organ tissue, and for generating a total conductivity readout;

d. means for periodically injecting a predetermined volume of a calibration fluid into a blood vessel in fluid communication with but spaced apart from the adjacent organ tissue;

e. calibration means for converting the total conductivity readout into a true local tissue blood flow readout or displacing said heat transfer means from the first location, said calibration means including i. recording means for recording the changes in the total conductivity readout caused by the passage of said calibration fluid by said heat transfer means;

ii. means for plotting a conductivity washout curve based on the recorded changes in the total conductivity readout to derive a total conductivity to true local blood flow correction factor; and iii. means for receiving the total conductivity readout and the total conductivity to true local blood flow correction factor and for computing and displaying a true local tissue blood flow readout representative of the true value of the local tissue blood flow at the first location in the organ tissue;

whereby the true local tissue blood flow readout may be displayed on a continuous basis to accurately quantify the local tissue blood flow at the first location on a real time basis.

2. The apparatus of claim 1 wherein said apparatus further includes second heat transfer means coupled to said control means and positionable at a second location in said tissue spaced apart from the first location and including means for maintaining said second heat transfer means fixed at the second location for converting a flow of electrical current into heat energy and for transferring the heat energy into a second region of adjacent organ tissue surrounding and located in close proximity to the second location for measuring the true value of local tissue blood flow at the second location.

3. The apparatus of claim 1 wherein said heat transfer means comprises a first thermistor.

4. The apparatus of claim 3 wherein said control means operates said thermistor in an isothermal mode to maintain a fixed temperature differential between said first thermistor and the adjacent organ tissue;

5. The apparatus of claim 3 wherein said control means operates said first thermistor in an isocaloric mode to transfer a fixed rate of heat flow into the adjacent organ tissue.

6. The apparatus of claim 3 wherein the organ tissue includes brain tissue, wherein a ventriculostomy tube having a semi-rigid body with a cylindrical cross section and a fluid transmissive passageway extending from a first end to a second end of said tube is inserted into the brain tissue, and wherein said first thermistor is coupled to the body of said ventriculostomy tube.

7. The apparatus of claim 6 wherein the first end of said ventriculostomy tube includes a port for establishing fluid communication between said port and the second end of said tube, wherein the brain tissue includes a lateral ventricle, and wherein the port of said ventriculostomy tube is inserted into the lateral ventricle.

8. The apparatus of claim 7 further including means coupled to the second end of said ventriculostomy tube for measuring intracranial pressure by sensing the fluid pressure level at the second end of said tube.

9. A method for measuring the true value of local tissue blood flow at a first location in an organ tissue wherein the first location resides outside of the interior of any blood vessels, said method comprising the steps of:
   a. inserting heat transfer means into the first location and maintaining the position of said heat transfer means fixed at the first location, the organ tissue surrounding and located in close proximity to said heat transfer means at the first location defining a region of adjacent organ tissue having an ambient temperature and a total conductivity;
   b. operating said heat transfer means in a non-self-heating mode to measure the ambient temperature of the adjacent organ tissue;
   c. reconfiguring said heat transfer means to operate in a self-heating mode at the first location;
   d. operating said heat transfer means in the self-heating mode to establish a temperature differential between said heat transfer means and the adjacent organ tissue for transferring heat energy from said heat transfer means to the adjacent organ tissue;
   e. measuring the quantity of heat energy transferred from said heat transfer means into the adjacent organ tissue;
   f. computing the total conductivity of the adjacent organ tissue as a function of the ambient temperature of the adjacent organ tissue and the heat energy transferred into the adjacent organ tissue and generating a total conductivity readout;
   g. calibrating the total conductivity readout to derive a true local tissue blood flow readout
      i. continuing to operate said heat transfer means in the self-heating mode at that first location and injecting a predetermined volume of a calibration fluid into a blood vessel in fluid communication with but spaced apart from the adjacent organ tissue;
      ii. recording the changes in the total conductivity readout caused by the passage of said volume of calibration fluid by said heat transfer means without displacing said heat transfer means from the first location;
      iii. plotting a conductivity washout curve based on the recorded changes in the total conductivity readout to derive a total conductivity to true local blood flow correction factor;
      iv. applying said correction factor to the total conductivity readout to generate and display a true local tissue blood flow readout representative of the true quantitative value of the local tissue blood flow at the first location in the organ tissue; and
   h. periodically recalibrating the true local tissue blood flow readout by periodically repeating the calibration step without displacing said heat transfer means from the first location;
whereby the true local tissue blood flow readout may be displayed on a continuous basis to accurately quantify the local tissue blood velocity at the first location on a real time basis.

10. The method of claim 9 wherein said heat transfer means comprises a first thermistor and wherein said first thermistor is isothermally operated in the self-heating mode to maintain a fixed temperature differential between said first thermistor and the adjacent organ tissue.

11. The method of claim 10 wherein said heat transfer means includes a second thermistor positioned at a second location within the organ tissue spaced apart from the first location and wherein the steps of claim 10 are repeated in connection with said second thermistor to generate a true local tissue blood flow readout representative of the true value of the local tissue blood flow at the second location.

12. The method of claim 9 wherein said heat transfer means comprises a first thermistor and wherein said first thermistor is operated isocalorically in the self-heating mode to transfer a fixed rate of heat flow into the adjacent organ tissue.

13. The method of claim 12 wherein said heat transfer means includes a second thermistor positioned at a second location in the organ tissue spaced apart from the first position and wherein the steps of claim 12 are repeated in connection with said second thermistor to generate a true local tissue blood flow readout representative of the true value of the local tissue blood flow at the second location.

14. The method of claim 9 wherein the organ tissue includes brain tissue, wherein a ventriculostomy tube having a semi-rigid body with a cylindrical cross section and a fluid transmissive passageway extending from a first end to a second end of said tube is inserted into the brain tissue, and wherein said heat transfer means is coupled to the body of said tube.

15. The method of claim 14 wherein the first end of said ventriculostomy tube includes a port for establishing fluid communication between said port and the second end of said tube.

16. The method of claim 15 wherein the brain tissue includes a lateral ventricle, and wherein the port of said ventriculostomy tube is inserted into the lateral ventricle.

17. The method of claim 16 including the further step of measuring intracranial pressure by continuously sensing the fluid pressure level at the second end of said tube.

* * * * *